United States Patent
Xia et al.

(10) Patent No.: US 10,261,005 B2
(45) Date of Patent: Apr. 16, 2019

(54) DETERMINING THE DENSITY AND VISCOSITY OF A FLUID USING AN ELECTROMAGNETIC FORCE CONTACTLESS DRIVEN DENSITOVISCOUS SENSOR

(71) Applicant: HALLIBURTON ENERGY SERVICES, INC., Houston, TX (US)

(72) Inventors: Hua Xia, Huffman, TX (US); Darren Gascooke, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 191 days.

(21) Appl. No.: 15/123,356

(22) PCT Filed: Feb. 20, 2015

(86) PCT No.: PCT/US2015/016882
§ 371 (c)(1),
(2) Date: Sep. 2, 2016

(87) PCT Pub. No.: WO2016/133542
PCT Pub. Date: Aug. 25, 2016

(65) Prior Publication Data
US 2017/0067809 A1 Mar. 9, 2017

(51) Int. Cl.
*G01N 9/00* (2006.01)
*E21B 49/08* (2006.01)
(Continued)

(52) U.S. Cl.
CPC ............ *G01N 11/16* (2013.01); *E21B 49/08* (2013.01); *E21B 49/10* (2013.01); *G01N 9/002* (2013.01);
(Continued)

(58) Field of Classification Search
CPC .............. G01N 11/167; G01N 9/002; G01N 2009/004; G01N 2009/006; G01N 27/725
See application file for complete search history.

(56) References Cited

U.S. PATENT DOCUMENTS 5,837,898 A 11/1998 MacLauchlan et al.
6,070,457 A 6/2000 Robinson
(Continued)

FOREIGN PATENT DOCUMENTS

WO 2010033532 3/2010
WO 2013165428 11/2013

OTHER PUBLICATIONS

International Patent Application No. PCT/US2015/016882, International Search Report and Written Opinion, dated Oct. 21, 2015, 17 pages.
(Continued)

*Primary Examiner* — Paul M. West
(74) *Attorney, Agent, or Firm* — Kilpatrick Townsend & Stockton LLP (57) ABSTRACT

A system is provided that can include a first tube for communicating a fluid through a wellbore. The system can also include a gap between the first tube and a first electromagnetic acoustic transducer (EMAT). The first EMAT can be positioned to magnetically couple with the first tube. The first EMAT can include a magnet and a wire coil positioned around the magnet. The first EMAT can coupled to a power source and positioned to, responsive to receiving a power from the power source, apply a first magnetic force to the first tube for determining a density or viscosity of the fluid.

22 Claims, 7 Drawing Sheets

(51) Int. Cl.
*E21B 49/10* (2006.01)
*G01N 11/00* (2006.01)
*G01N 11/16* (2006.01)
*G01N 27/72* (2006.01)

(52) U.S. Cl.
CPC .......... *G01N 11/00* (2013.01); *G01N 11/167* (2013.01); *G01N 27/725* (2013.01); *E21B 2049/085* (2013.01); *G01N 2009/004* (2013.01); *G01N 2009/006* (2013.01); *G01N 2011/0086* (2013.01)

(56) References Cited

U.S. PATENT DOCUMENTS

| | | |
|---|---|---|
| 6,688,176 B2 | 2/2004 | Storm, Jr. et al. |
| 7,150,317 B2 | 12/2006 | Barolak et al. |
| 7,311,143 B2 | 12/2007 | Engels et al. |
| 7,562,587 B2 | 7/2009 | Atkinson et al. |
| 7,574,898 B2 | 8/2009 | Harrison et al. |
| 7,697,375 B2 | 4/2010 | Reiderman et al. |
| 7,784,330 B2 | 8/2010 | Angelescu et al. |
| 7,874,199 B2 | 1/2011 | Chaudoreille et al. |
| 8,037,765 B2 | 10/2011 | Reiderman |
| 8,484,003 B2 | 7/2013 | Hsu et al. |
| 8,485,018 B2 | 7/2013 | Kawamura et al. |
| 2002/0178803 A1 | 12/2002 | Pelletier et al. |
| 2012/0227483 A1 | 9/2012 | Kruspe et al. |

OTHER PUBLICATIONS

European Patent Application No. 15882868.1, Extended European Search Report dated Sep. 3, 2018, 8 pages.

DETERMINING THE DENSITY AND VISCOSITY OF A FLUID USING AN ELECTROMAGNETIC FORCE CONTACTLESS DRIVEN DENSITOVISCOUS SENSOR

CROSS-REFERENCE TO RELATED APPLICATIONS

This is a U.S. national phase under 35 U.S.C. 371 of International Patent Application No. PCT/US2015/016882, titled "Determining the Density and Viscosity of a Fluid using and Electromagnetic Force Contactless Driven Densitoviscous Sensor" and filed Feb. 20, 2015, the entirety of which is incorporated herein by reference.

TECHNICAL FIELD

The present disclosure relates generally to devices for use in well systems. More specifically, but not by way of limitation, this disclosure relates to determining the density and viscosity of a downhole fluid using an electromagnetic force contactless driven densitoviscous sensor.

BACKGROUND

A well system (e.g., an oil or gas well) can include a wellbore drilled into a subterranean formation. These wells may have oil, water, and gas fluids. These fluids may be in multi-phase mixtures, such as mixtures of water, gaseous hydrocarbons, and fluidic hydrocarbons. Each phase may have a different density, viscosity, compressibility, elasticity, and acoustic impedance. In order to evaluate the commercial value of such a hydrocarbon producing well, it can be useful to analyze the thermophysical properties of the formation fluid in-situ.

Different physical sensors (e.g., a capacitance sensor, sonic sensor, or resistivity sensor) or chemical analytical sensing instruments (e.g., an optical fluid analyzer) can be packaged into a downhole tool for analyzing well fluid. One example of a downhole tool for analyzing well fluid can be a reservoir description tool (RDT). The RDT can include sensors for analyzing various physical and chemical properties of the downhole fluid. The sensors can include a densitometer for determining the density of the fluid.

DETAILED DESCRIPTION

Certain aspects and features of the present disclosure are directed to a system for determining the density and viscosity of a fluid using an electromagnetic force driven vibrating tube as a densitoviscous sensor. The densitoviscous sensor can be magnetically coupled to (e.g., capable of applying a magnetic force to), but not contacting, the tube. In some examples, the densitoviscous sensor can be included in a downhole logging tool. For example, the densitoviscous sensor and the tube can be included in a reservoir description tool (RDT) for simultaneous downhole fluid density and viscosity in-situ analysis.

The densitoviscous sensor can include an electromagnetic acoustic transducer (EMAT). The EMAT can include a magnet and a wire coil positioned (e.g., wrapped) around the magnet. A portion of the wire coil can be positioned within the EMAT. Another portion of the wire coil can be positioned outside the EMAT and in the gap between the EMAT and the tube. Each coil can consist of N wire loops.

The wire coil within the EMAT can be coupled to a power source. To operate the EMAT, the power source can transmit a power signal to the wire coil. The power signal can include both a time-modulated amplitude and a frequency-modulated carrier signal. The wire coil can receive the power signal from the power source. As current from the power signal flows through the wire coil, an Eddy current can be induced on the surface of the tube. The Eddy current can flow in a direction opposite the direction of the current flowing through the wire coil. The combination of the magnetic field generated by the magnet and the Eddy current flowing along the surface of the tube can generate Lorentz forces on the tube. The Lorentz forces can push and pull the tube in a direction perpendicular to the longitude of the tube, which can vibrate the tube.

The vibration of the tube can cause current to be induced within the wire coil. A current meter coupled to the wire coil can detect the amplitude of the induced current. The power source can modulate the frequency of the power signal until the current meter determines that the amplitude of the induced current is at a maximum (described in greater detail below). The amplitude of the induced current can be at its maximum when the tube is vibrating at its resonance frequency. The power source may transmit a signal associated with the resonance frequency of the tube to a computing device.

The computing device can be communicatively coupled to the power source, and can receive the signal associated with the resonance frequency of the tube. The resonance frequency of the tube can be based on the fluid in the tube. For example, the resonance frequency of the tube can be different if the fluid is oil than if the fluid is water. Based on the resonance frequency of the tube, the computing device can determine the density of the fluid. For example, the computing device can apply the resonance frequency to one or more algorithms (described below) to determine the density of the formation fluid.

In some examples, the computing device can additionally or alternatively determine the viscosity of the formation fluid in the tube. The computing device can determine the viscosity of the fluid by causing the power source to stop transmitting the power signal for a period of time. Upon the power source no longer transmitting the power signal to the tube, the vibrations in the tube can decay, for example, due to fluid friction effects with the tube's inner wall. The rate at which the vibrations in the tube decay can depend on the fluid in the tube. For example, the free vibrations of the tube can decay at a different rate if the fluid is water than if the fluid is oil because of different elastic energy dissipations due to friction. As the vibrational energy of the tube dissipates, the amplitude of the current induced in the wire coil can decline as a function of time. The declining current amplitudes can be transmitted to the computing device. The computing device can determine a characteristic (e.g., a slope or curve) associated with the declining amplitudes. For example, the computing device can plot the declining amplitudes and determine the slope of the decline. Based on the characteristic, the computing device can determine the viscosity of the fluid. For example, the computing device can consult a lookup table and correlate the characteristic with a viscosity.

As still another example, the computing device can determine the viscosity of the fluid based on a quality factor (Q) of the system. Because the viscosity of the fluid in the tube can affect the quality factor of the system, the computing device can use the quality factor to determine the viscosity of the fluid. For example, the computing device can receive a signal associated with the induced current in the wire coil. The computing device can perform a Discrete Fourier Transform on the signal to determine an associated frequency spectrum or power spectral density. Based on the frequency spectrum of the signal, the computing device can determine characteristics of the signal (e.g., the resonance frequency and its linewidth at the 3 dB bandwidth). The computing device can apply the characteristics to one or more algorithms (described below) to determine the quality factor of the system. The computing device can determine the viscosity of the fluid based on the quality factor variation of the fluid. For example, the computing device can consult a lookup table and correlate a differential quality factor variation with a viscosity.

In some examples, multiple EMATs can be positioned around the tube. The EMATs can be symmetrically positioned. The EMATs can be synchronously operated such that the tube is vibrated in the same direction. For example, one EMAT can be positioned above the tube and can be operated to apply a pushing force on the tube. Another EMAT can be positioned below the tube and can be operated to apply a pulling force on the tube. The EMATs can work together to move vibrate the tube in the same direction.

Figure 4:
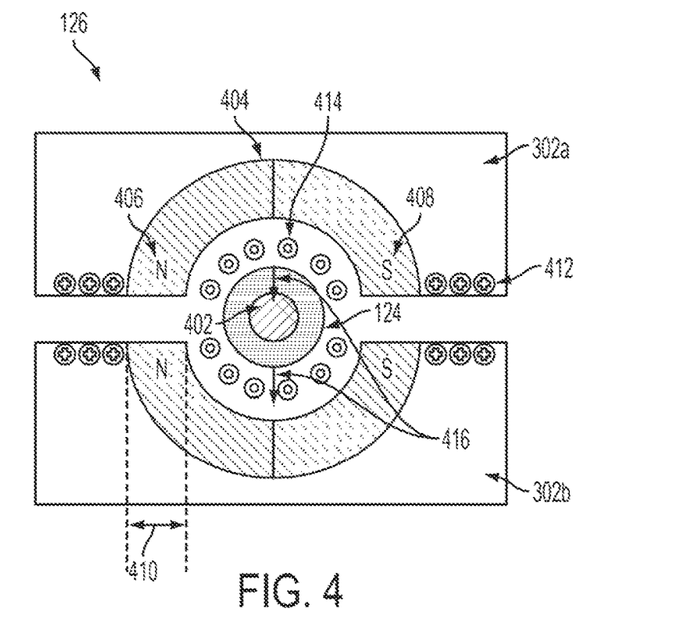
FIG. 4 is a cross-sectional end view of an electromagnetic force contactless driven densitoviscous sensor using a single tube for determining the density and viscosity of a fluid according to one example.

In some examples, a pair of EMATs can be positioned around two or more tubes. The EMATs can be symmetrically positioned around the tubes, for example, as described in further detail with respect to FIG. 4B. The EMATs can be synchronously operated such that the tubes are vibrated in the same direction. In some examples, one tube can include the target fluid for density and viscosity analysis. A second tube can include a calibration fluid. The calibration fluid can be sealed inside the second tube. The computing device can calibrate density and viscosity measurements associated with the target fluid against the density and viscosity measurements associated with the calibration fluid in the second tube. This can help compensate for any measurement errors resulting from temperature and pressure variations downhole. In some examples, the difference between the density and viscosity measurements associated with the tubes can be used for multi-phase analysis, for example, near a water zone or a gas zone in a well system.

In some examples, the densitoviscous sensor can allow a well operator to determine both the density and the viscosity of the fluid with a single tool. Density and viscosity can be determined substantially simultaneously. This can also allow well tools that may not have previously included a viscosity sensor (e.g., due to space or monetary constraints) to be able to determine viscosities. The density and viscosity of the fluid can be used to determine the type of fluid (e.g., gas, oil, or water) present in the formation, and to further evaluate the economic viability of a well (e.g., for well exploration and petroleum production optimization).

In some examples, the densitoviscous sensor can also be more sensitive than traditional sensors to multi-phase fluids, which can lead to more accurate density and viscosity determinations when multi-phase fluids are flowing through the tube. The densitoviscous sensor can also have an increased lifespan over traditional densitometers by applying symmetric forces to the tube (e.g., if two symmetrically placed EMATs are used), rather than asymmetric forces to the tube. Further, the densitoviscous sensor can determine the viscosity and density of fluid in harsh environmental conditions. For example, the densitoviscous sensor can determine the viscosity and density for fluid while in a downhole environment that has a temperature of 350° F. (or more) and 25,000 psi (or more) of pressure.

In some examples, the initial fluid extracted from the wellbore could be contaminated (e.g., by mud), which can affect the density of the fluid in the tube. After a period of time, the level of contamination in the fluid may decrease, making the fluid more suitable for physical and chemical analysis. Therefore, it can be desirable to determine the level of contamination in the fluid. In some examples, the computing device can determine the contamination level of the formation fluid. The computing device can determine the density of the fluid by vibrating the tube at its resonant frequency. As the level of contamination of the fluid changes (e.g., due to diminished mud contamination within the formation fluid), the measured density can change. The rate at which density changes can depend on the level of contaminants in the fluid. For example, the computing device can plot the changing density of the fluid as a function of time. Based on the plot, the computing device may be able to estimate when the contamination concentration has reduced below a threshold (e.g., below 5%). Based on the contamination level and the density of the contaminant, the computing device can determine the density of the fluid. For example, the computing device can consult lookup table and correlate the density of the fluid with different hydrocarbon fluid densities (e.g., water can be 1000 kg/m$^3$, mud can be 1000 kg/m$^3$, and oil can be 700 kg/m$^3$). A real-time density analysis can help predict pumping time for a well operator to manage open-hole logging service tasks.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

Figure 1:
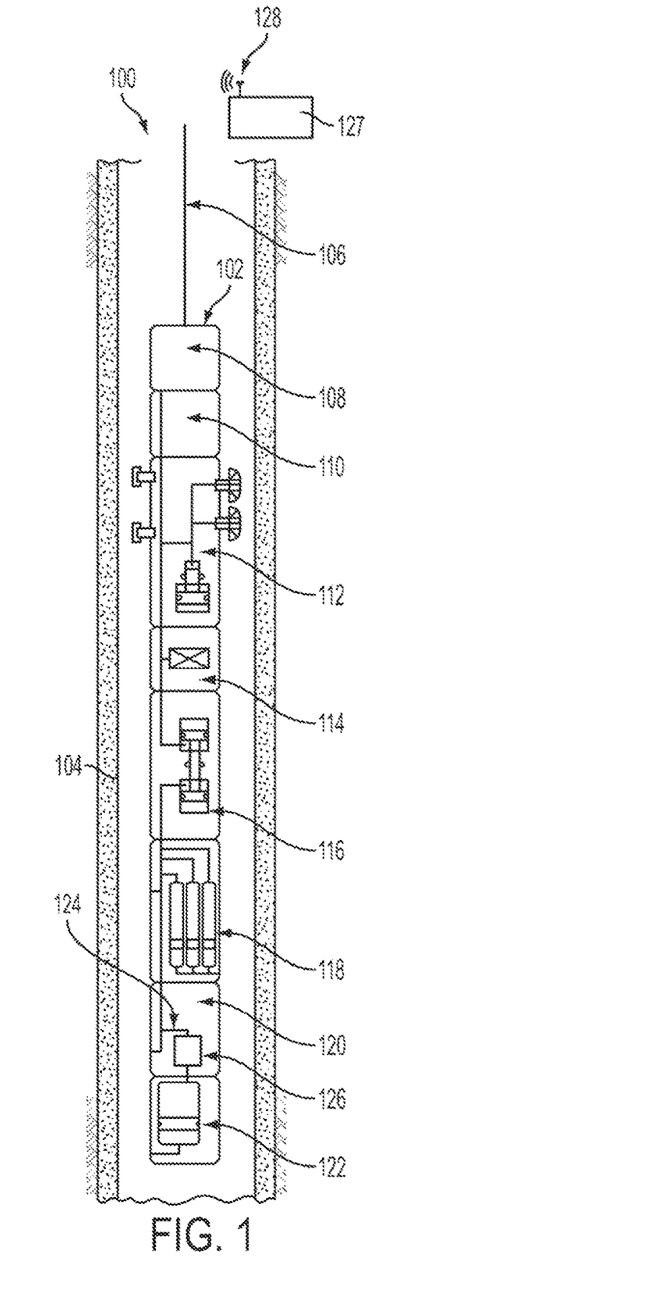
FIG. 1 is a cross-sectional view of a well system for determining the density and viscosity of a fluid using an electromagnetic force contactless driven densitoviscous sensor according to one example.

FIG. 1 is a cross-sectional view of a well system 100 for determining a density and viscosity of a fluid using an electromagnetic force contactless driven vibrating tube as a densitoviscous sensor 126 according to one example. The well system 100 (e.g., an oil or gas well for extracting fluids from a subterranean formation) can include a wellbore 104 drilled from a formation. In some examples, the wellbore 104 can be cased and cemented, as shown in FIG. 1. In other examples, the wellbore 104 can be uncased or the casing may not be cemented. In one example, the wellbore 104 can be in its production stage.

The well system 100 can include a well tool 102. The well tool 102 can be positioned in the wellbore 104 via a wireline 106, slickline, or coiled tubing. In some examples, well tool 102 can include a logging tool. The well tool 102 can include one or more modules for determining the characteristics of the wellbore 104, a fluid within the wellbore 104, or the formation (e.g., the physical makeup of the formation, or its electrical, acoustic, or electromagnetic properties). For example, the well tool 102 can include a telemetry module 108 for communicating power and data between the well tool 102 and another well system 100 component (e.g., computing device 127). The well tool 102 can also include a hydraulic power module 110 for converting electrical power to hydraulic power, a probe module 112 for sampling formation fluids, a fluid test module 114 for performing tests on a fluid, a flow control module 116 for controlling the flow of fluid through the well tool 102, a sample collection module 118 for storing collected fluid samples, and other modules 120, 122.

The well system 100 can include one or more tubes 124 for communicating fluid through the well system 100. A densitoviscous sensor 126 can be magnetically coupled to a portion of a tube 124. The densitoviscous sensor 126 can be positioned in the well tool 102 or elsewhere in the well system 100. For example, if the well system 100 is in its production stage, the tube 124 can be a production tube and the densitoviscous sensor 126 can be magnetically coupled to the production tube. As another example, the densitoviscous sensor 126 can be integrated with other sensors (e.g., a sensor for determining the multi-phase composition of a fluid, a sensor for determining mud filtrate contamination, and a temperature sensor). The densitoviscous sensor 126 can determine the density and viscosity of fluid in the tube 124.

The well system 100 can include a computing device 127 for operating the densitoviscous sensor 126. In some examples, the computing device 127 can operate a power source (not shown) coupled to the densitoviscous sensor 126. The computing device 127 can be positioned at the surface of the wellbore 104, below ground, or offsite. The computing device 127 can include a processor interfaced with other hardware via a bus. A memory, which can include any suitable tangible (and non-transitory) computer-readable medium, such as RAM, ROM, EEPROM, or the like, can embody program components that configure operation of the computing device 127. In some examples, the computing device 127 can include input/output interface components (e.g., a display, keyboard, touch-sensitive surface, and mouse) and additional storage.

The computing device 127 can communicate with other well system 100 components via a communication device 128. For example, the computing device 127 can communicate with the densitoviscous sensor 126, a power source coupled to the densitoviscous sensor 126, a current meter coupled to the densitoviscous sensor 126, and the well tool 102 via the communication device 128. The communication device 128 can represent one or more of any components that facilitate a network connection. In the example shown in FIG. 1, the communication device 128 is wireless and can include wireless interfaces such as IEEE 1002.11, Bluetooth, or radio interfaces for accessing cellular telephone networks (e.g., transceiver/antenna for accessing a CDMA, GSM, UMTS, or other mobile communications network). In other examples, the communication device 128 can be wired and can include interfaces such as Ethernet, USB, IEEE 1394.

The computing device 127 can be electrically coupled to a signal processor (not shown). The signal processor can be internal or external to the computing device 127. The signal processor can process a signal received by the computing device 127 (e.g., from the densitoviscous sensor 126, a power source coupled to the densitoviscous sensor 126, a current meter coupled to the densitoviscous sensor 126, or the well tool 102). Processing the signal can include amplifying the signal, filtering (e.g., low-pass, band-pass, or high-pass filtering) the signal, inverting the signal, performing one or more mathematical operations on the signal (e.g., performing a Fourier transform on the signal), improving the signal-to-noise ratio of the signal, and otherwise preparing the signal for use by the computing device 127.

Figure 2:
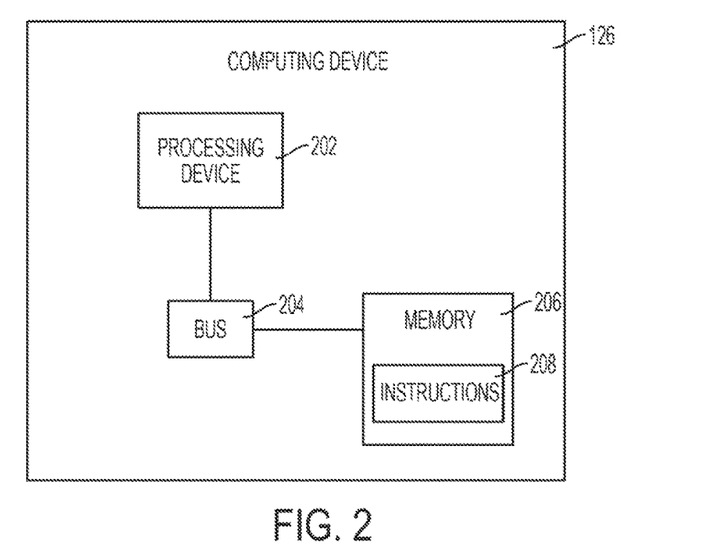
FIG. 2 is a block diagram showing an example of a computing device for determining the density and viscosity of a fluid using an electromagnetic force contactless driven densitoviscous sensor according to one example.

FIG. 2 is a block diagram depicting an example of a computing device 127 for determining the density and viscosity of a fluid using an electromagnetic force contactless driven densitoviscous sensor according to one example. The computing device 127 includes a processing device 202, a memory device 206, and a bus 204.

The processing device 202 can execute one or more operations for determining the density and viscosity of a fluid using a densitoviscous sensor. The processing device 202 can execute instructions 208 stored in the memory device 206 to perform the operations. The processing device 202 can include one processing device or multiple processing devices. Non-limiting examples of the processing device 202 include a Field-Programmable Gate Array ("FPGA"), an application-specific integrated circuit ("ASIC"), a microprocessor, etc.

The processing device 202 can be communicatively coupled to the memory device 206 via the bus 204. The non-volatile memory device 206 may include any type of memory device that retains stored information when powered off. Non-limiting examples of the memory device 206 include electrically erasable and programmable read-only memory ("EEPROM"), flash memory, or any other type of non-volatile memory. In some aspects, at least some of the memory device 206 can include a medium from which the processing device 202 can read the instructions 208. A computer-readable medium can include electronic, optical, magnetic, or other storage devices capable of providing the processing device 202 with computer-readable instructions or other program code. Non-limiting examples of a computer-readable medium include (but are not limited to) magnetic disk(s), memory chip(s), ROM, random-access memory ("RAM"), an ASIC, a configured processor, optical storage, or any other medium from which a computer processor can read instructions. The instructions may include processor-specific instructions generated by a compiler or an interpreter from code written in any suitable computer-programming language, including, for example, C, C++, C#, etc.

Figure 3:
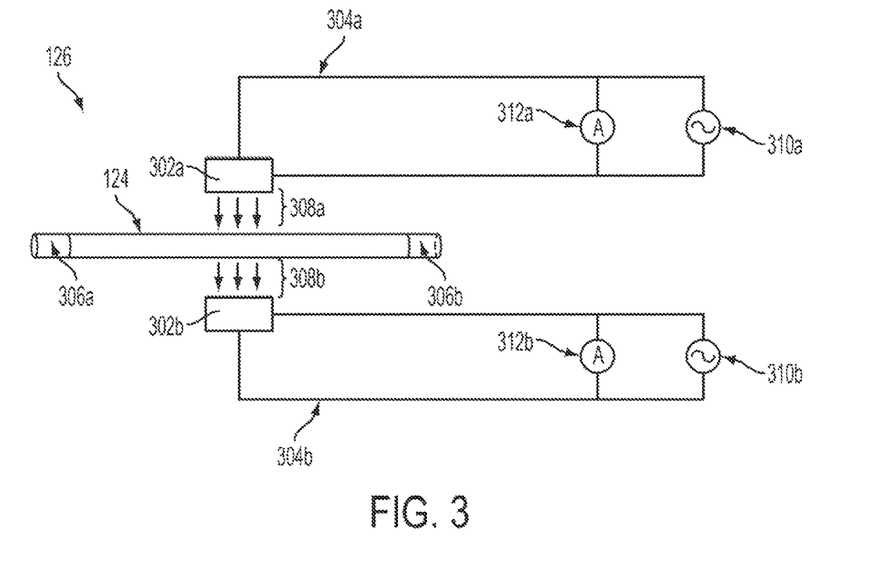
FIG. 3 is a schematic diagram of an electromagnetic force contactless driven densitoviscous sensor for determining the density and viscosity of a fluid according to one example.

FIG. 3 is a schematic diagram of an electromagnetic force contactless driven densitoviscous sensor 126 for determining the density and viscosity of a fluid according to one example. The densitoviscous sensor 126 can include an EMAT 302a, 302b. The EMAT 302a, 302b can be positioned near a portion of the tube 124. For example, the EMAT 302a, 302b can be near, but not contacting (e.g., spaced from), a portion of the tube 124. This can form a gap 308a, 308b between the EMAT 302a, 302b and the tube 124. In some examples, the gap 308a, 308b can be 0.5 mm to 1.0 mm in size. In other examples, the gap 308a, 308b can include any spacing in which the EMAT 302a, 302b can impart a sufficient Lorentz force on the tube 124 to vibrate the tube 124 (discussed below). The EMAT 302a, 302b can be positioned in the longitudinal center of the tube 124, or elsewhere along the longitude of the tube 124.

The tube 124 can have any longitudinal length and have any diameter sufficient for determining the density and viscosity of a fluid flowing through the tube 124. In one example, the longitudinal length of the tube 124 can be between 100 mm and 200 mm, and the diameter can be between 2 mm and 4 mm. The tube 124 can include any suitable material, such as a titanium alloy or carbon fiber reinforced tube. Fluid can flow in either direction through the tube 124. In some examples, the tube 124 can include a coupling device 306a, 306b for mechanically coupling the tube 124 to another component. In one example, the coupling device 306a, 306b can be configured to couple the tube 124 to another tube or well system component. The coupling device 306a, 306b can include a Swagelok fitting, a latch, a fastener, or a threaded bore.

The EMAT 302a, 302b can be electrically coupled to one or more power sources 310a, 310b via wires 304a, 304b. The power source 310a, 310b can provide power for operating the EMAT 302a, 302b. The power source 310a, 310b can be positioned at the surface of the wellbore, in a well tool (e.g., well tool 102 of FIG. 1), or elsewhere. In some examples, the power source 310a, 310b can be integrated with the EMAT 302a, 302b into a single unit.

In some examples, the power source 310a, 310b can be operated by, and in communication with, a computing device (e.g., computing device 127 of FIG. 1). For example, the power source 310a, 310b can include a communication device (e.g., the communication device 128 of FIG. 1) for communicating with the computing device. Upon receiving power from a power source 310a, 310b, the EMAT 302a, 302b can exert a magnetic force on the tube 124. The magnetic force can push the tube 124 away from, or pull the tube 124 towards, the EMAT 302a, 302b. This can cause the tube 124 to vibrate. In FIG. 3, the magnetic forces are depicted as arrows in the gap 308a, 308b between the EMAT 302a, 302b and the tube 124. The vibration of the tube 124 can be used to determine the density and viscosity of fluid flowing through the tube 124 (discussed in greater detail below).

The EMAT 302a, 302b can also be electrically coupled to a current meter 312a, 312b. The current meter 312a, 312b can detect an amount of current associated with the EMAT 302a, 302b. The current meter 312a, 312b can be positioned at the surface of the wellbore, in a well tool, or elsewhere. In some examples, the current meter 312a, 312b can be integrated with the power source 310a, 310b, the EMAT 302a, 302b, or both into a single unit. The current meter 312a, 312b can be operated by, and in communication with, a computing device. For example, the current meter 312a, 312b can include a communication device for communicating with the computing device.

In some examples, the densitoviscous sensor 126 can include multiple EMATs 302a, 302b. The gap 308a, 308b between each EMAT 302a, 302b and the tube 124 can be the same or can be different. Each of the EMATs 302a, 302b can be positioned in the longitudinal center of the tube 124 or elsewhere along the longitude of the tube 124. The EMATs 302a, 302b can be positioned symmetrically around the tube 124 or asymmetrically around the tube 124. In some examples, each of the EMATs 302a, 302b can be operated such that they vibrate the tube 124 in the same direction. For example, as shown in FIG. 3, one EMAT 302a can be operated for applying a pushing force on the tube 124, while another EMAT 302b can be operated for applying a pulling force on the tube 124.

FIG. 4 is a cross-sectional end view of an electromagnetic force contactless driven densitoviscous sensor 126 for determining the density and viscosity of a fluid according to one example. As described above, the densitoviscous sensor 126 can include at least one EMAT 302a, 302b positioned near a tube 124 for applying magnetic forces to the tube 124. The EMAT 302a, 302b can include a "C"-like shape or a "half-donut" shape for encircling a portion of the tube 124. Fluid 402 can flow through the tube 124.

The EMAT 302a, 302b can include a magnet 404. The magnet 404 can include a north magnetic pole 406 and a south magnetic pole 408. In some examples, the magnet 404 can include samarium-cobalt (Sm—CO) or other permanently magnetic material. The magnet 404 can have any suitable wall thickness 410. The wall thickness 410 can include the difference between the inner diameter of the magnet 404 and the outer diameter of the magnet 404. In one example, the magnet 404 can have a wall thickness of 12.7 mm. As the wall thickness 410 of the magnet 404 increases, the Lorentz force generated by the EMAT 302a, 302b (discussed in greater detail below) can increase. The magnet 404 can have a high magnetic strength for generating a sufficient Lorentz force when the EMAT 302a, 302b is operated.

The EMAT 302a, 302b can include one or more wire coils positioned around the magnet 404. For example, the EMAT 302a, 302b can include one wire coil wrapped around the north magnetic pole 406 and another wire coil wrapped around the south magnetic pole 408. The wire coil can include any suitable material, such as tungsten, platinum, copper, or gold. The wire coils can include any suitable diameter, such as a diameter between 0.1 mm and 1.0 mm.

Figure 5:
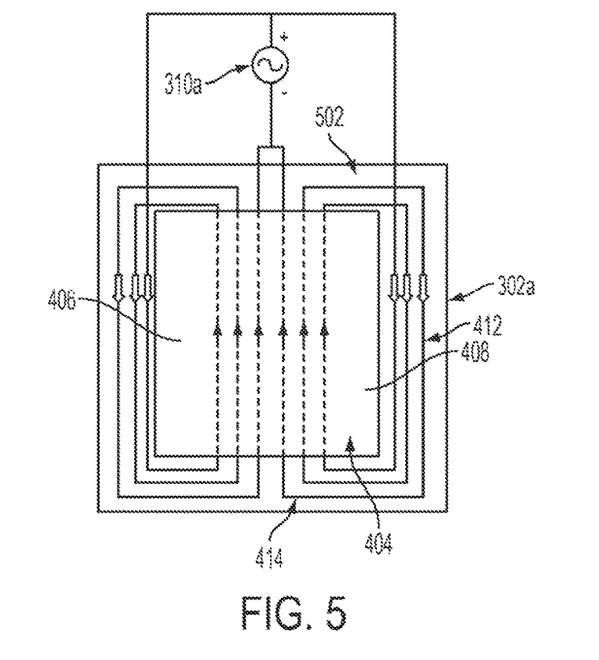
FIG. 5 is a cross-sectional end view of an electromagnetic force contactless driven densitoviscous sensor for differential density and viscosity measurement according to one example.

The wire coil can include a first portion 412, which can be positioned within the EMAT 302a, 302b. Current can flow in a first direction (e.g., the direction out of the page) in the first portion 412. The wire coil can also include a second portion 414, which can be positioned in the gap between the EMATs 302a, 302b and the tube 124. Current in the second portion 414 can flow in a direction opposite the first direction (e.g., the direction into the page). For example, as shown in the cross-sectional top view depicted in FIG. 5, a wire coil 502 can be wrapped around the south magnetic pole 408 of the magnet 404. A power source 310a can transmit current through the first portion 412 of the wire coil 502, around an end of the south magnetic pole 408, and through the second portion 414 of the wire coil 502.

Returning to FIG. 4, the wire coil can be coupled to a power source (e.g., power source 310a or 310b of FIG. 3). If the EMAT 302a, 302b includes multiple wire coils, the wire coils can be coupled to the same power source or to different power sources. The power source can transmit current to the wire coil. Upon the current flowing through the wire coil, an Eddy current can be induced on the surface of the tube 124. The Eddy current can flow in a direction opposite the direction of the current flowing through the wire coil. The relationship between the current flowing through the wire coil and the Eddy current can be represented as:

$$I_e(t) = -\zeta \cdot N \cdot I(t), \text{ where } 0 < \zeta \leq 1$$

where $I_e(t)$ is the Eddy current, $\zeta$ is an Eddy current induction coefficient, N is the number of loops in a wire coil, and I(t) is the driving current flowing through the wire coil. Although the wire coil in FIG. 4 only depicts three wire loops, any number of wire loops that can generate sufficient Lorentz forces 416 can be used. In some examples, a higher number of wire loops may enhance the efficiency of the electromagnetic induction.

The combination of the magnetic field generated by the magnet 404 (which can be perpendicular to the longitude of the tube 124) and the Eddy current flowing along the surface of the tube 124 can generate Lorentz forces 416. The total Lorentz force (F) produced can be represented as:

$$F(t) = F1(t) + F2(t) = 2 \cdot I_e(t) \times B$$

where F1(t) is the Lorentz force generated by the EMAT 302a on the tube 124, F2(t) is the Lorentz force generated by the EMAT 302b on the tube 124, $I_e(t)$ is the Eddy current, and B is the magnetic field of the magnet 404. The Lorentz forces 416 can push and pull the tube 124, which can vibrate the tube 124 in a direction perpendicular to the longitude of the tube 124. The vibration frequency and amplitude of the tube 124 can depend on, and be used to determine, the density and viscosity of a fluid in the tube 124.

Figure 6:
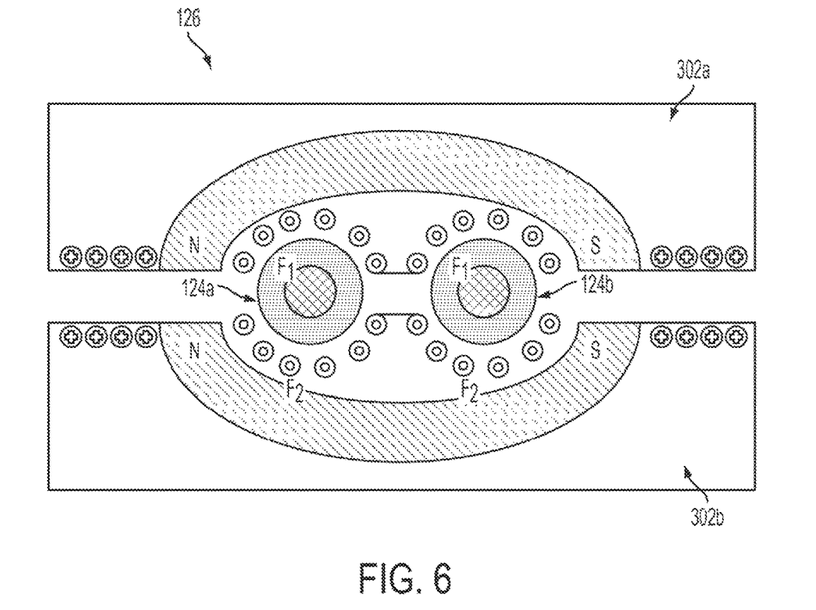
FIG. 6 is a cross-sectional top view of an electromagnetic force contactless driven densitoviscous sensor for determining the density and viscosity of a fluid according to one example.

FIG. 6 is a cross-sectional end view of an electromagnetic force contactless driven densitoviscous sensor 126 for differential density and viscosity measurement according to one example. The densitoviscous sensor 126 can include two tubes 124a, 124b for determining differential density and viscosity measurements.

For example, one tube 124a can include the target fluid (e.g., oil or gas) for density and viscosity analysis. The other tube 124b can include a calibration fluid, (e.g., deionized water) which can have a known density and viscosity. A power source can be used to actuate the densitoviscous sensor. The resulting viscosity and density measurements can be differential measurements generated due to the two tubes 124a, 124b. The differential measurement can mitigate variations due to fluctuating downhole temperatures, pressures, and multi-phase fluid flows. This can make the viscosity and density measurements more accurate.

The wire coils in each of the EMATS 302a, 302b can be positioned around both tubes 124a, 124b. Although the wire coils in FIG. 6 only depict four wire loops, any number of wire loops that can generate sufficient Lorentz forces can be used. In some examples, the number of wire loops can be an ideal number for optimizing the quality factor of the densitoviscous sensor 126.

Figure 7:
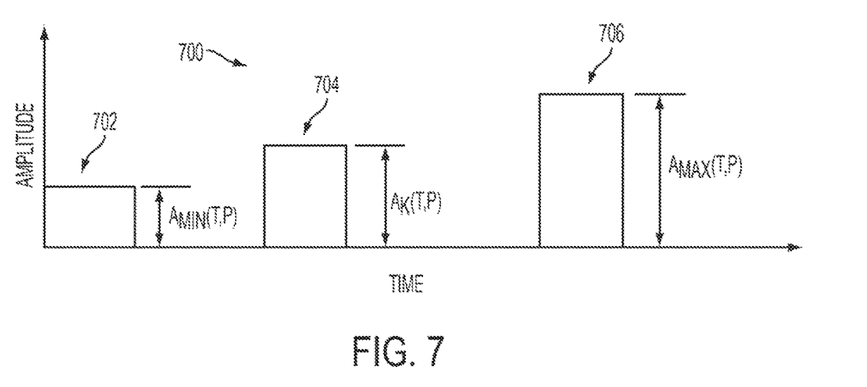
FIG. 7 is a graph depicting an example of a power signal for use with an electromagnetic force contactless driven densitoviscous sensor for determining the density of a fluid according to one example.

FIG. 7 is a graph depicting an example of a power signal 700 for use with a densitoviscous sensor for determining the density of a fluid according to one example. As described above, a power source can operate an EMAT by transmitting a power signal 700 to the wire coil within the EMAT, which can cause the tube to vibrate. In some examples, the power signal 700 can include a square wave. The vibration of the tube can cause current to be induced within the wire coil. A current meter coupled to the wire coil can detect the amplitude of the current in the wire coil.

The power source can modulate the amplitude of the power signal 700. For example, the power source can generate the power signal 700 with a high amplitude 706. This can excite the tube, causing a vertical displacement of a few hundred micrometers. As the amplitude of the power signal 700 changes, the amplitude with which the tube vibrates can change (e.g., proportionally). For example, as the frequency of the power signal 700 is increased from one amplitude 702 to a higher amplitude 704, the amplitude of the vibrations of the tube can increase at its fluid-dependent vibration frequency. In some examples, higher amplitude power signals may be used to vibrate the tube when the tube includes a heavy fluid (e.g., asphaltenes or wax-dominated fluid).

As the frequency with which the tube vibrates is stabilized at the tube's resonance frequency, the amplitude of the current induced in the wire coil can gradually approach its maximum amplitude. For example, as the frequency of the vibration of the tube approaches the resonance frequency of the tube, the perpendicular displacement of the tube during each oscillation can increase. This can bring the tube closer to the EMAT, which can increase the induced current in the wire coil. As another example, if the frequency of the vibration of the tube exceeds the resonance frequency of the tube, the perpendicular displacement of the tube during each oscillation can decrease. This can move the tube farther from the EMAT, which can decrease the induced current in the wire coil. Using these principles, the power source can modulate amplitude of the power signal 700 (e.g., to different amplitudes 702, 704, 706) until the current meter determines that the amplitude of the current in the wire coil is at its maximum. This can indicate that the tube is vibrating at its resonance frequency.

The resonance frequency of the tube can be based on the fluid in the tube. For example, the resonance frequency of the tube can be different if the fluid is oil than if the fluid is water or a fluid containing asphaltenes. The resonance frequency of the tube can be transmitted by the power source to a computing device (e.g., computing device 127 of FIG. 1). The computing device can apply the resonance frequency to one or more algorithms to determine the density of the fluid in the tube. For example, the computing device can apply the resonance frequency to the equation:

$$\rho(f) = A + B^*(a/f^2)$$

where $\rho(f)$ is the density of the fluid in the tube, A and B are calibration constants, and $\omega = 2^*\pi^*f$ is the angular resonance frequency of the tube. The calibration constants A and B can be based on a known substance. For example, water can be positioned in the tube and the calibration constants A and B can be adjusted until the density p(f) equals 1000 kg/m³. In one example, the computing device can further determine the type of the fluid (e.g., oil or water). The computing device can apply the density to a lookup table (e.g., stored in memory) to determine the associated fluid type.

Figure 8:
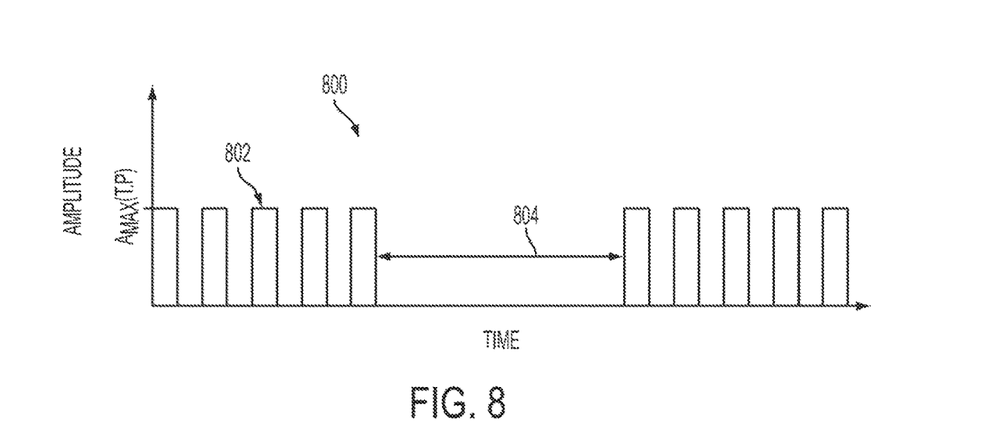
FIG. 8 is a graph depicting another example of a power signal for use with an electromagnetic force contactless driven densitoviscous sensor for determining the viscosity of a fluid according to one example.

FIG. 8 is a graph 800 depicting another example of a power signal for use with an electromagnetic force contactless driven densitoviscous sensor for determining the viscosity of a fluid according to one example. In some examples, the computing device can determine the viscosity of the fluid by causing the power source to stop transmitting the power signal 802 for a period of time 804 (e.g., 0.5 to 10 seconds). Upon the power source no longer transmitting power to the wire coil, the EMAT may stop generating Lorentz forces on the tube. With no Lorentz forces being applied to the tube, the mechanical structure of the tube (and fluid within the tube) can cause the vibrations of the tube to decay. The rate at which the vibrations of the tube decay can depend on the fluid in the tube. For example, the vibrations of the tube can decay at a different rate if the fluid is water than if the fluid is oil. As the vibrations of the tube decay, the amplitude of the current induced in the wire coil can decline. The current meter can detect the declining current amplitudes, voltages, or both and transmit them to the computing device.

The computing device can receive the current amplitudes from the current meter and apply them to one or more algorithms to determine the viscosity of the fluid in the tube. For example, the computing device can plot the declining current amplitudes and determine a curve associated with the plot. The computing device can apply the characteristics of the curve to lookup table to determine an associated fluid type and viscosity. The lookup table can associate curve characteristics with fluid types and viscosities.

In some examples, the computing device can cause the power source to output a power signal 802 (to the densitometer) with varying amplitudes and a resonant frequency associated with the resonant frequency of the tube. For example, as shown in FIG. 7, the power signal 700 can include three different amplitudes 702, 704, 706 and have a frequency that is the resonance frequency of the tube. Each different amplitude 702, 704, 706 in the power signal 700 can cause the densitoviscous sensor to apply a different strength magnetic force to the tube. The combination of the strength of the magnetic force applied to the tube and the fluid in the tube can affect how the tube vibrates (e.g., the vertical displacement of the tube). For example, heavier fluids, such as water (e.g., which can have a density of 1000 kg/m$^3$), may dampen the vibrations in the tube more than lighter fluid, such as gas (e.g., which can have a density of 1 kg/m$^3$). Thus, a high-amplitude power signal may cause the tube to vibrate with a large displacement if the tube includes gas, while the same high-amplitude power signal may cause the tube to vibrate with less vertical displacement if the tube includes water. Because the amount of current induced in the wire coil can be based on the amount of vertical displacement in the vibrations, the combination of the amplitude of the power signal 700 and the fluid in the tube can affect the current induced in the wire coil.

For each different amplitude 702, 704, 706 in the power signal 700, the current meter can measure the amplitude of the current induced in the wire coil and transmit the current measurement to the computing device. Based on the current measurements, the computing device can apply one or more algorithms to determine viscosity of the fluid. For example, the computing device can apply the current measurements that were taken at the different power signal 700 amplitudes (e.g., the different amplitudes 702, 704, 706 of the power signal 700) to the following set of equations:

$$A_1(T, P, t) = A_{01} * e^{(-\alpha_1 \cdot t)}$$

$$A_2(T, P, t) = A_{02} * e^{(-\alpha_2 \cdot t)}$$

$$\ldots$$

$$A_k(T, P, t) = A_{0k} * e^{(-\alpha_k \cdot t)}$$

$$\ldots$$

$$A_N(T, P, t) = A_{0N} * e^{(-\alpha_N \cdot t)}$$

where $A_N(T, P, t)$ is the measured response from the current meter, T is downhole temperature, P is the well tool differential pressure, t is time, $A_{0N}$ is the power signal 700 amplitude, and $\alpha_N$ is the decay rate. By combining the measured current amplitudes and time responses, the decay rate can be related to (e.g., proportional to) the viscosity of the fluid. To determine the viscosity of the fluid, the computing device can determine the averaged decay rate ($\alpha_{ave}$) using the following equation:

$$\alpha_{ave}(1/N \cdot t) * \Sigma_{(i=1, \ldots N)} \text{Ln}(A_{0i}/A_i(T,P,t))$$

The computing device can apply the averaged decay rate to the equation $A_0(T, P, t) = A(0)*e^{(-\alpha_{ave} \cdot t)}$, which can be used to solve the damping equation of the fluid:

$$m\frac{d^2 A}{dt^2} = -kx - D(\eta)\frac{dA}{dt}$$

where m is the fluid mass, k is the stiffness coefficient of the vibrating tube, and $D(\eta) \approx \eta \cdot S/h$ (where $\eta$ is the viscosity of the fluid, S is the surface area of the fluid interacting with the tube, h is the effective thickness of the viscous fluid layer). Solving the damping equation of the fluid can yield a viscous variation trend associated with the fluid. The computing device can compare the viscous variation trend against calibration data (e.g., a calibration trend) to determine the viscosity of the fluid. The calibration data can be generated using a standard calibration fluid, such as water.

In some examples, the computing device can determine the quality factor of the tube. Because the viscosity of the fluid can affect the quality factor of the tube, the computing device can use the quality factor to determine the viscosity of the fluid (and the type of the fluid). For example, the quality factor of the tube can be represented by the following equation:

$$Q = \omega(0) * m/D(\eta)$$

where $\omega(0)$ is the fundamental frequency of the system, m is the fluid mass, and as described above, $D(\eta)$ is roughly equivalent to $\eta \cdot S/h$ (where $\eta$ is the viscosity of the fluid, S is the surface area of the fluid interacting with the tube, h is the effective thickness of the viscous fluid layer). Thus, there can be a mathematical relationship between the viscosity of the fluid and the quality factor Q.

Figure 9:
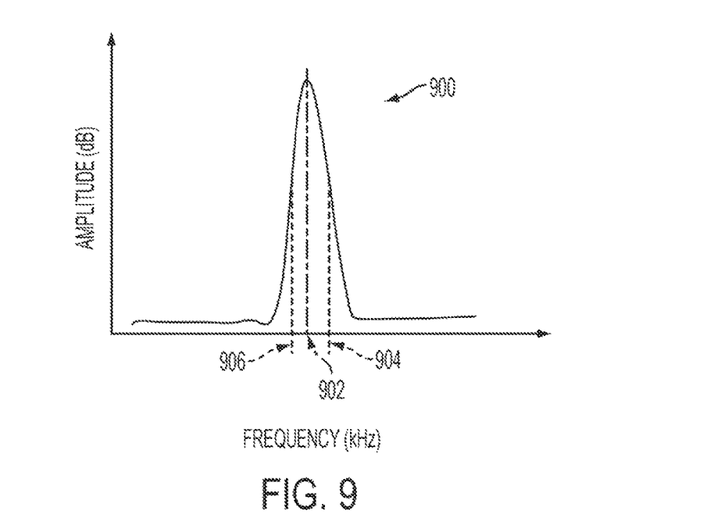
FIG. 9 is a graph depicting an example of a frequency spectrum of a current associated with an electromagnetic force contactless driven densitoviscous sensor according to one example.

To determine the quality factor of the tube, the computing device can perform a Discrete Fourier Transform (DFT) using the current amplitudes to determine an associated frequency spectrum. As shown in FIG. 9, the frequency spectrum can include a waveform with a resonance frequency 902. The computing device can determine a 3 dB bandwidth ($\Delta f$) of the waveform by subtracting the low cutoff frequency 906 from the high cutoff frequency 904. If the low cutoff frequency 906 and the high cutoff frequency 904 are in radians, the 3 dB bandwidth can be expressed as:

$$\Delta f = (\omega_H - \omega_L)/2\pi$$

where $\Delta f$ is the 3 dB bandwidth, $\omega_H$ is the high cutoff frequency 904 in radians, and $\omega_L$ is the low cutoff frequency 906 in radians. The low cutoff frequency 906 and the high cutoff frequency 904 can be the frequencies below and above the resonance frequency 902, respectively, at which the amplitude of the waveform is 3 dB lower than amplitude of the waveform at the resonance frequency 902. The computing device can apply the resonance frequency 902 and the $\Delta f$ to one or more equations to determine the quality factor of the tube. For example, the computing device can apply the resonance frequency 902 and the $\Delta f$ to the equation:

$$Q(t) = f_0/\Delta f$$

where $Q(t)$ is the quality factor of the tube at time t, $f_0$ is the resonance frequency 902, and $\Delta f$ is the 3 dB bandwidth. The computing device can then apply $Q(t)$ to the equation:

$$\Delta Q = Q(t) - Q(0)$$

where $Q(t)$ is the quality factor of the tube at time t, $Q(0)$ is a calibration constant, and $\Delta Q$ is the change between $Q(t)$ and $Q(0)$. In some examples, the calibration constant $Q(0)$ can be determined by calculating the quality factor of the tube using a reference calibration tube 124b (e.g., as shown in FIG. 6), or when there is a known fluid in the tube (e.g., water). The computing device can apply $\Delta Q$ to a lookup table to determine to determine an associated fluid type and viscosity. The lookup table can associate changes in quality factor ($\Delta Q$) with fluid types and viscosities.

In some examples, the computing device can use multiple methods for determining the viscosity of the fluid for redundancy or to improve accuracy. For example, the computing device can use both the declining current amplitude approach and the quality factor approach to determine the viscosity of the fluid. The computing device can compare the results of both approaches to determine the validity of the results. If the results of the two approaches are different, the computing device can determine that an error occurred.

Figure 10:
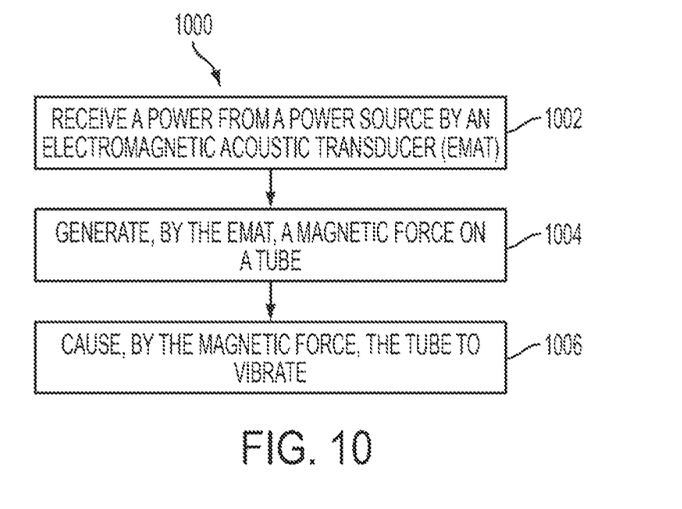
FIG. 10 is an example of a flow chart of a process for determining the density and viscosity of a fluid using an electromagnetic force contactless driven densitoviscous sensor according to one example.

FIG. 10 is an example of a flow chart of a process 1000 for determining the density and viscosity of a fluid using an electromagnetic force contactless driven densitoviscous sensor according to one example.

In block 1002, an EMAT receives power from a power source. In some examples, the power can include one or more pulses of power with varying amplitudes (e.g., as shown in FIG. 7). For example, the power can include a square waveform, generated over a period of time, with enough energy to vibrate the tube at a resonance frequency.

The EMAT can include a magnet and a wire coil wrapped around the magnet. The wire coil can be electrically coupled to the power source. For example, the wire coil can be electrically coupled to the power source via a wire. The wire coil can receive power from the power source. The EMAT may not be contacting, but can be magnetically coupled to, one or more tubes in a wellbore. For example, the EMAT can be magnetically coupled to one or two tubes in a downhole logging service tool.

In block 1004, the EMAT generates a magnetic force on the tube. The power transmitted from the power source can cause current to flow in the wire coil. This can generate an Eddy current on the surface of the tube. The Eddy current combined with the magnetic field of the magnet can generate the magnetic force on the tube.

In block 1006, the magnetic force causes the tube to vibrate. For example, the magnetic force can push and pull the tube upwards and downwards, respectively, which can vibrate the tube in a direction perpendicular to the longitude of the tube. The vibration of the tube can be used to determine the density and viscosity of a fluid in the tube.

Figure 11:
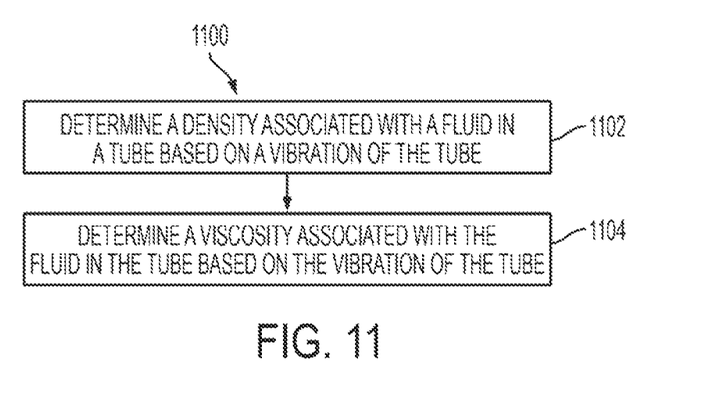
FIG. 11 is an example of a flow chart of a process for determining the density and viscosity of a fluid using an electromagnetic force contactless driven densitoviscous sensor according to one example.

FIG. 11 is an example of a flow chart of a process 1100 for determining the density and viscosity of a fluid using an electromagnetic force contactless driven densitoviscous sensor according to one example.

In block 1102, a computing device that is communicatively coupled to the EMAT determines the density associated with a fluid in the tube. For example, the computing device can determine the resonance frequency of the tube based on the vibration of the tube. The resonance frequency of the tube can be based on the fluid in the tube. The computing device can use the resonance frequency of the tube to determine the density of the fluid in the tube.

In block 1104, the computing device determines a viscosity associated with the fluid in the tube based on the vibration of the tube. For example, the computing device can cause the power source to stop transmitting power to the tube. This can cause the vibrations in the tube to decrease. The computing device can determine a mathematical curve associated with the decreasing vibrations. The computing device can use the curve to determine the viscosity of the fluid in the tube. For example, the computing device can apply the characteristics of the curve to a lookup table to determine an associated viscosity.

As another example, the computing device can determine a quality factor associated with the tube. The quality factor can change based on the fluid in the tube. The computing device can determine the quality factor by dividing a resonance frequency associated with the tube a 3 dB bandwidth associated with the tube. The computing device can use the quality factor to determine the viscosity of the fluid in the tube. For example, the computing device can apply the quality factor to a lookup table to determine an associated viscosity.

Figure 12:
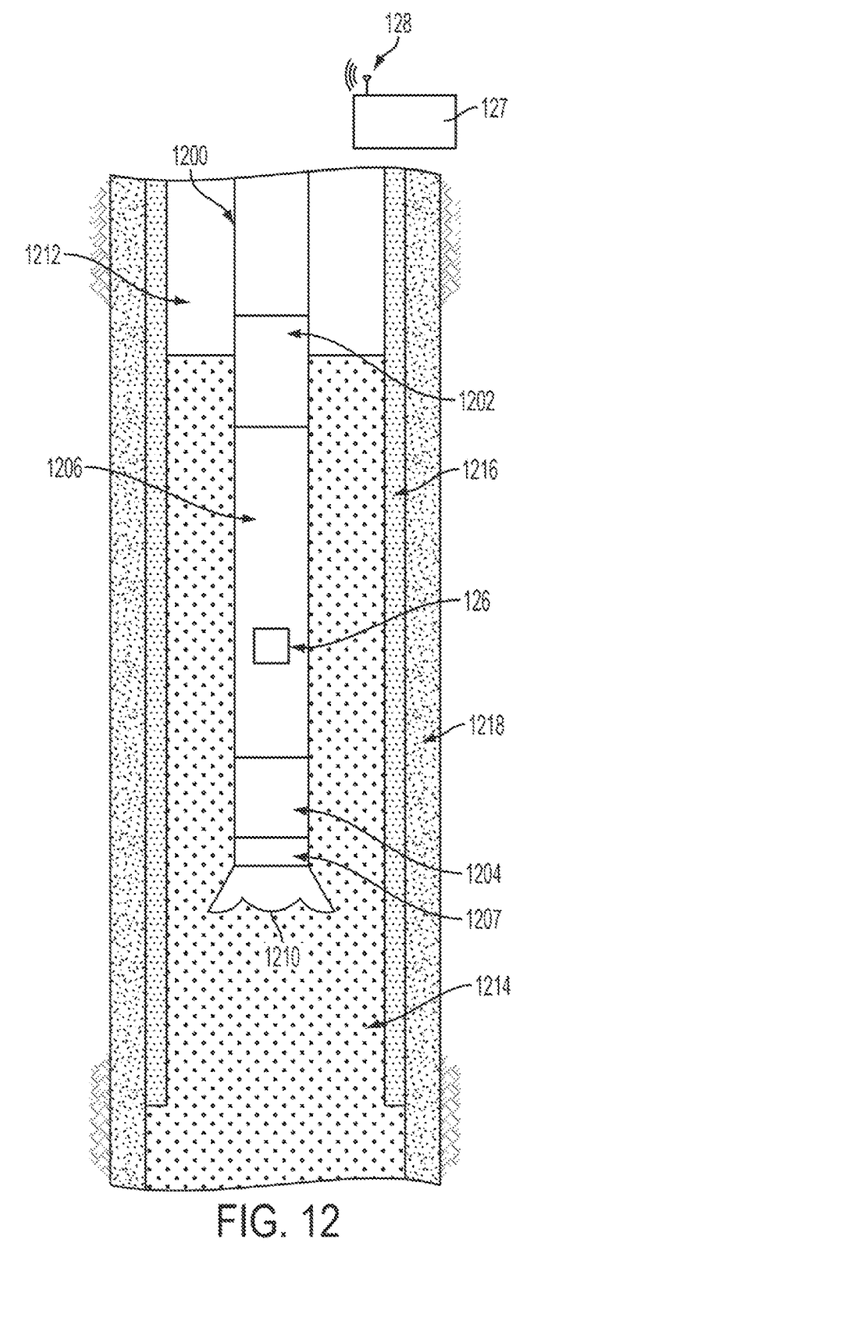
FIG. 12 is a cross-sectional view of another well system for determining the density and viscosity of a fluid using an electromagnetic force contactless driven densitoviscous sensor according to one example.

FIG. 12 is a cross-sectional view of another well system for determining the density and viscosity of a fluid 1214 using an electromagnetic force contactless driven densitoviscous sensor according to one example. In this example, the well system includes a wellbore. The wellbore can include a casing string 1216 and a cement sheath 1218. In some examples, the wellbore can include fluid 1214. The fluid 1214 (e.g., mud or a hydrocarbon) can flow in an annulus 1212 positioned between a well tool 1200 and a wall of the casing string 1216 (or the wellbore).

A well tool 1200 (e.g., logging-while-drilling tool) can be positioned in the wellbore. The well tool 1200 can include various subsystems 1202, 1204, 1206, 1207. For example, the well tool 1200 can include a subsystem 1202 that includes a communication subsystem. The well tool 1200 can also include a subsystem 1204 that includes a saver subsystem or a rotary steerable system. A tubular section or an intermediate subsystem 1206 (e.g., a mud motor or measuring-while-drilling module) can be positioned between the other subsystems 1202, 1204. In some examples, the well tool 1200 can include a drill bit 1210 for drilling the wellbore. The drill bit 1210 can be coupled to another tubular section or intermediate subsystem 1207 (e.g., a measuring-while-drilling module or a rotary steerable system).

The well tool 1200 can include one or more tubes (not shown) for communicating fluid through the well system 100. A densitoviscous sensor 126 can be magnetically coupled to a portion of a tube. The densitoviscous sensor 126 can be positioned on or inside in the well tool 1200.

The well system can include a computing device 127 for operating the densitoviscous sensor 126. In this example, the computing device 127 is positioned at the surface of the wellbore 104. However, as discussed above with respect to FIG. 1, the computing device 127 may also be positioned elsewhere in the well system. The computing device 127 can communicate with other well system components via a communication device 128.

In some aspects, a system for determining the density and viscosity of a fluid using an electromagnetic force contactless driven densitoviscous sensor is provided according to one or more of the following examples:

Example #1

A system can include a first tube for communicating a fluid through a wellbore. The system can also include a gap between the first tube and a first electromagnetic acoustic transducer (EMAT). The system can also include the first EMAT. The first EMAT can be positioned to magnetically couple with the first tube. The first EMAT can include a magnet and a wire coil positioned around the magnet. The first EMAT can be coupled to a power source and positioned to, responsive to receiving a power from the power source, apply a first magnetic force to the first tube for determining a density or viscosity of the fluid.

Example #2

The system of Example #1 may feature the gap being less than 1.0 mm.

Example #3

The system of any of Examples #1-2 may feature the first EMAT including a C-like shape for positioning the first EMAT around a diameter of the first tube.

Example #4

The system of any of Examples #1-3 may feature the system including a second EMAT. The second EMAT can be positioned to magnetically couple with the first tube. The second EMAT can be coupled to the power source and positioned to, responsive to receiving the power from the power source, apply a second magnetic force to the first tube for determining the density or the viscosity of the fluid.

Example #5

The system of Example #4 may feature the first EMAT and the second EMAT being positioned symmetrically around a diameter of the first tube.

Example #6

The system of any of Examples #4-5 may feature the system further including a second tube. The second tube can include a calibration fluid. The first EMAT can be positioned to magnetically couple with the second tube and to, responsive to receiving the power from the power source, apply a third magnetic force to the second tube. The second EMAT can be positioned to magnetically couple with the second tube and to, responsive to receiving the power from the power source, apply a fourth magnetic force to the second tube.

Example #7

The system of any of Examples #4-6 may feature the first EMAT being positioned to apply the first magnetic force to the first tube to cause the first tube to vibrate, and the second EMAT being positioned to apply the second magnetic force to the first tube to cause the first tube to vibrate.

Example #8

The system of any of Examples #1-7 may feature the first EMAT being positioned to apply the first magnetic force to the first tube to generate an induced current in the wire coil for determining the viscosity of the fluid.

Example #9

The system of any of Examples #1-8 may feature the first EMAT being coupleable to a current meter for determining an amplitude of the induced current.

Example #10

The system of Example #9 may feature the viscosity of the fluid being determinable based on a decay rate associated with the first tube, a quality factor associated with the first tube, or a curve associated with the amplitude of the induced current.

Example #11

The system of any of Examples #1-10 may feature the first EMAT and the first tube being positioned in a downhole logging tool.

Example #12

An electromagnetic acoustic transducer (EMAT) can include a magnet and a wire coil. The wire coil can be coupled to a power source. The wire coil can be positioned around the magnet to apply, responsive to receiving power to the wire coil, a first magnetic force to a first tube disposed in a wellbore to determine a density or a viscosity of a fluid in the first tube. A gap can be between the EMAT and the first tube.

Example #13

The EMAT of Example #12 may feature the gap being less than 1.0 mm.

Example #14

The EMAT of any of Examples #12-13 may feature the EMAT being positioned to apply the first magnetic force to the first tube to vibrate the first tube at a resonance frequency.

Example #15

The EMAT of any of Examples #12-14 may feature wire coil being positioned to receive apply a second magnetic force to a second tube in the wellbore for determining the density or the viscosity of the fluid in the first tube.

Example #16

The EMAT of any of Examples #12-15 may feature the EMAT being positioned to apply the first magnetic force to the first tube to generate an induced current in the wire coil. The viscosity of the fluid can be determinable based on both a decay rate and a quality factor associated with the first tube, or an amplitude associated with the induced current.

Example #17

The EMAT of any of Examples #12-16 may feature the EMAT being positioned in a downhole logging tool.

Example #18

A method can include receiving, by an electromagnetic acoustic transducer (EMAT), a power from a power source. The EMAT can include a magnet and a wire coil. The wire coil can be positioned around the magnet and electrically coupled to the power source. There can be a first gap between the EMAT and a first tube in a wellbore. The method can also include generating, by the EMAT, a first magnetic force on the first tube. The method can further include causing, by the first magnetic force, a vibration of the first tube. The vibration can be used to determine a density associated with a fluid in the first tube.

Example #19

The method of Example #18 may feature determining, by a computing device communicatively coupled to the EMAT, the density associated with the fluid in the first tube based on the vibration of the first tube. The method may also feature determining, by the computing device, a viscosity associated with the fluid in the first tube based on a decay rate and a quality factor associated with the vibration of the first tube.

Example #20

The method of any of Examples #18-19 may feature a second gap being positioned between the EMAT and a second tube in the wellbore. The method may also feature generating, by the EMAT, a second magnetic force on the second tube. The method may further feature causing, by the second magnetic force, a second vibration of the second tube. The second vibration can be used to mitigate measurement errors due to a change in a downhole temperature, a downhole pressure, or a characteristic of a multi-phase fluid.

Example #21

The method of any of Examples #18-20 may feature the EMAT being disposed in the wellbore via a wireline, a coiled tube, or a slickline.

Example #22

The method of any of Examples #18-21 may feature the EMAT being disposed in the wellbore via a drill string.

Example #23

The method of Example #22 may feature the drill string being included in a logging while drilling tool.

The foregoing description of certain embodiments, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system, comprising:
   a first tube for communicating a fluid through a wellbore;
   a first electromagnetic acoustic transducer (EMAT) positioned to magnetically couple with the first tube, the first EMAT comprising:
   a magnet; and
   a wire coil positioned around the magnet;
   wherein the first EMAT is configured to receive power from a power source and responsively apply a first magnetic force to the first tube for determining a density or a viscosity of the fluid; and
   a second EMAT that is positioned to magnetically couple with the first tube, wherein the second EMAT is configured to receive power from the power source and responsively apply a second magnetic force to the first tube.

2. The system of claim 1, wherein a gap is disposed between the first tube and the first EMAT, the gap-being less than 1.0 mm.

3. The system of claim 1, wherein the first EMAT comprises a C-like shape for positioning the first EMAT around an exterior of the first tube.

4. The system of claim 1, wherein the first EMAT and the second EMAT are positioned symmetrically around an exterior of the first tube.

5. The system of claim 4, further comprising a second tube having a calibration fluid, wherein:
   the first EMAT is positioned to magnetically couple with the second tube and to apply a third magnetic force to the second tube in response to power from the power source; and
   the second EMAT is positioned to magnetically couple with the second tube and to apply a fourth magnetic force to the second tube in response to power from the power source.

6. The system of claim 1, wherein the first EMAT is positioned to apply the first magnetic force to the first tube to cause the first tube to vibrate, and the second EMAT is positioned to apply the second magnetic force to the first tube to cause the first tube to vibrate.

7. The system of claim 1, wherein the first EMAT is positioned to apply the first magnetic force to the first tube to generate an induced current in the wire coil for determining the viscosity of the fluid.

8. The system of claim 7, wherein the first EMAT is coupleable to a current meter for determining an amplitude of the induced current.

9. The system of claim 8, wherein the viscosity of the fluid is determinable based on a decay rate associated with the first tube, a quality factor associated with the first tube, or a curve associated with the amplitude of the induced current.

10. The system of claim 1, wherein the first EMAT and the first tube are positioned in a downhole logging tool.

11. A system comprising:
    an electromagnetic acoustic transducer (EMAT) having a C-like shape for positioning the EMAT around at least a portion of an exterior of a first tube, the EMAT including:
    a magnet; and
    a wire coil positioned around the magnet;
    wherein the EMAT is configured to apply a first magnetic force to the first tube in response to power to determine a density or a viscosity of a fluid in the first tube.

12. The system of claim 11, wherein a gap is disposed between the first tube and the first EMAT, the gap-being less than 1.0 mm.

13. The system of claim 11, wherein the EMAT is positioned to apply the first magnetic force to the first tube to vibrate the first tube at a resonance frequency.

14. The system of claim 11, wherein the wire coil is positioned to apply a second magnetic force to a second tube for determining the density or the viscosity of the fluid in the first tube.

15. The system of claim 11, wherein the EMAT is positioned to apply the first magnetic force to the first tube to generate an induced current in the wire coil, and wherein the viscosity of the fluid is determinable based on both a decay rate and a quality factor associated with the first tube, or an amplitude associated with the induced current.

16. The system of claim 11, wherein the EMAT is positioned in a downhole logging tool.

17. A method comprising:
receiving, by a wire coil of an electromagnetic acoustic transducer (EMAT), power from a power source, wherein the EMAT has a C-like shape positioned around at least a portion of an exterior of a first tube, and wherein the EMAT comprises a magnet and the wire coil positioned around the magnet;
generating, by the EMAT, a first magnetic force on the first tube in response to the power from the power source; and
causing, by the first magnetic force, a vibration of the first tube, wherein the vibration is usable to determine a density associated with a fluid in the first tube.

18. The method of claim 17, further comprising:
determining, by a computing device communicatively coupled to the EMAT, the density associated with the fluid in the first tube based on the vibration of the first tube; and
determining, by the computing device, a viscosity associated with the fluid in the first tube based on a decay rate and a quality factor associated with the vibration of the first tube.

19. The method of claim 18, wherein there is a first gap between the EMAT and the first tube and a second gap between the EMAT and a second tube, and further comprising:
generating, by the EMAT, a second magnetic force on the second tube; and
causing, by the second magnetic force, a second vibration of the second tube, wherein the second vibration is usable to mitigate measurement errors due to a change in a downhole temperature, a downhole pressure, or a characteristic of a multi-phase fluid.

20. The method of claim 18, further comprising disposing the EMAT in a wellbore via a wireline, a coiled tube, or a slickline.

21. The method of claim 18, further comprising disposing the EMAT in a wellbore via a drill string.

22. The method of claim 21, wherein the drill string is included in a logging while drilling tool.

* * * * *